United States Patent [19]

Soper

[11] 3,990,879

[45] Nov. 9, 1976

[54] METHOD OF CONTROLLING AQUATIC WEEDS

[75] Inventor: Quentin Francis Soper, Indianapolis, Ind.

[73] Assignee: Eli Lilly and Company, Indianapolis, Ind.

[22] Filed: Dec. 26, 1974

[21] Appl. No.: 536,497

[52] U.S. Cl. .................................... 71/66; 71/90; 260/306.8 D
[51] Int. Cl.² ............................................ A01N 9/12
[58] Field of Search ......................... 71/90, 66, 67

[56] References Cited
UNITED STATES PATENTS 3,822,280 7/1974 Moser et al. .................... 71/90 X
3,827,875 8/1974 Krenzer ................................ 71/90

OTHER PUBLICATIONS

Kubo et al. J. Agr. Food Chem. vol. 18, 1970, pp. 60–65.

*Primary Examiner*—Lewis Gotts
*Assistant Examiner*—Catherine L. Mills
*Attorney, Agent, or Firm*—Dwight E. Morrison; Everet F. Smith

[57] ABSTRACT

A method of controlling aquatic weeds which comprises adding to a body of water containing the aquatic weeds a substituted 1-thiadiazolyl-3-arylurea in sufficient quantity to kill the weeds.

9 Claims, No Drawings

METHOD OF CONTROLLING AQUATIC WEEDS

BACKGROUND OF THE INVENTION

1. Field of the Invention

The field of the invention relates to the control of aquatic weeds in canals, rivers, ponds, lakes and impoundments.

2. Description of the Prior Art

The problems of controlling the growth of organisms in aqueous systems are serious and growing in severity. Submerged aquatic weeds, for example, cause major problems in water distribution and irrigation systems. The growth of weeds in irrigation canals greatly reduces the conductivity and capacity of such systems with resulting substantial economic loss. Large sums are therefore being spent in the mechanical and other methods of removal of weed growths from irrigation canals, especially in the southern and western parts of the United States.

Because of the great difficulties involved in the mechanical removal of weeds and other undesired forms of aquatic life from irrigation canals, ponds, lakes, impoundments, etc., it has been proposed to utilize chemical control. Accordingly, various types of chemicals have been added to such bodies of water.

In the prior art, Offenlegungsschrift No. 2,017,842 (Nov. 5, 1970), teaches the use of some thiadiazoleureas substituted in the 5-position of the thiadiazole ring with alkenylthio, alkynylthio, and other substituted thio substituents. The compounds are alleged to be terrestrial growth regulators and herbicides. There is no teaching that the compounds are useful against aquatic weeds and none of the tests described in the document suggest the compounds would be active as aquatic herbicides. In addition, the compounds are structurally different from those included within the scope of the instant application.

Also in the prior art is Dutch Patent No. 69,06983 (Nov. 25, 1969), which teaches 1,3,4-thiadiazolylureas having, inter alia, a trifluoromethyl group in the 5-position of the thiadiazole ring and an aryl or substituted aryl group attached to the urea nitrogen farthest removed from the thiadiazole ring. These Dutch compounds are taught as being useful as either total or selective terrestrial herbicides when applied pre- or postemergent against weeds in cotton and grain crops. The compounds also are taught as being active against snails, phytopathogenic fungi, insects and mites. However, there is no teaching that the compounds would be active as aquatic herbicides.

In addition, British Patent No. 1,250,624 (Oct. 20, 1971), teaches a series of compounds useful in biocidal preparations, one of which compounds is identified as 1-(1,3,4-thiadiazol-2-yl)-3-($\alpha,\alpha,\alpha$-trifluoro-p-tolyl)urea. The biocidal preparations are alleged to act as general microbiocides useful to protect timber, wool, paper, textiles, plastics, hides, synthetic fibers, rubber, dyestuffs, or dyepastes, building materials, adhesives, oils, waxes, cork, cosmetics and detergents against damage by bacteria and fungi. The compounds are also alleged to act as ingested agents in plant protection, as agents against tapeworms, liver flukes, nematodes and anopheles (larvae), against the various excitants of coccidiosis, as timber protection agents in storage protection, as anticaries agents, as chemical sterilizing agents, and against mollusks, lampreys, tube-dwelling worms, mussels, algae, hydroids, water snails and land snails, termites, ticks, amoeba, schistosomes, salmonellae, trichomonads, filaria, protozoa, plasmodia, trematodes, trypanosomes, viruses and the like. However, there is no teaching that the compounds would be active against or useful in the control of aquatic weeds.

The search for an effective aquatic herbicide continues, since there exists a very distinct need for a method of controlling the growth of aquatic weeds.

SUMMARY OF THE INVENTION

The present invention relates to a method of controlling aquatic weeds by adding to the water containing such aquatic weeds an herbicidally-effective amount of substituted 1-thiadiazolyl-3-arylurea.

DESCRIPTION OF THE PREFERRED EMBODIMENT

This invention relates to a novel method for the control of aquatic weeds. More particularly, this invention relates to a novel method and compositions for the control of aquatic weeds using compounds of the formula

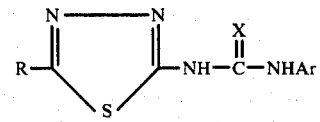

wherein
R is hydrogen, $C_1$–$C_{10}$ alkyl, halo ($C_1$–$C_2$)alkyl, phenyl, nitro, hexylthio, hexylsulfonyl, or halo;
Ar is phenyl, or phenyl having one or more substituents, up to five, selected from the group consisting of methyl, nitro, trifluoromethyl, methoxy, cyano, and halo; and
X is oxygen or sulfur.

In the above formula, $C_1$–$C_{10}$ alkyl is a saturated straight- or branched-chain hydrocarbon radical such as methyl, ethyl, n-propyl, isopropyl, n-butyl, isobutyl, sec.-butyl, t-butyl, n-amyl, sec.-amyl, isoamyl, t-amyl, n-hexyl, isohexyl, sec.-hexyl, n-heptyl, isoheptyl, sec.-heptyl, n-octyl, sec.-octyl, isooctyl, n-nonyl, isononyl, n-decyl, isodecyl, 1,1-dimethyloctyl, and the like.

Halo is chloro, bromo, iodo, and fluoro.

Halo($C_1$–$C_2$)alkyl is illustratively trifluoromethyl, chlorodifluoromethyl, dichloromethyl, tetrafluoroethyl, pentafluoroethyl, and the like.

Phenyl having one or more substituents selected from the group consisting of methyl, nitro, trifluoromethyl, methoxy, cyano and halo is illustratively 3,4-dichlorophenyl, 3,4-dibromophenyl, $\alpha,\alpha,\alpha$-trifluoro-p-tolyl, o-tolyl, m-tolyl, p-tolyl, $\alpha,\alpha,\alpha$-trifluoro-m-tolyl, m-nitrophenyl, $\alpha,\alpha,\alpha$-trifluoro-o-tolyl, o-nitrophenyl, $\alpha,\alpha,\alpha$-trifluoro-2-nitro-p-tolyl, p-methoxyphenyl, p-nitrophenyl, 3,4-xylyl, $\alpha,\alpha,\alpha,\alpha',\alpha',\alpha'$-hexafluoro-3,5-xylyl, 2,6-dichlorophenyl, p-cyanophenyl, 2,4-dichlorophenyl, 3,4,5-trichlorophenyl, p-fluorophenyl, o-fluorophenyl, m-fluorophenyl, 4-chloro-$\alpha,\alpha,\alpha$-trifluoro-m-tolyl, 3-chloro-4-fluorophenyl, 3,6-dichlorophenyl, 2,4-dibromophenyl, 2,6-dibromophenyl, 3,5-difluorophenyl, 3,4-difluorophenyl, 3,4-diiodophenyl, 2,6-diiodophenyl, 3,4,5-tribromophenyl, 3,4,5-trifluorophenyl, 3,4,5-triiodophenyl, p-chlorophenyl, p-bromophenyl, p-iodophenyl, o-chlorophenyl, m-chlorophenyl, m-iodophenyl, m- methoxyphenyl, m-cyanophenyl, o-cyanophenyl, pentachlorophenyl, and the like.

The thiadiazol-2-ylurea compounds useful in the novel method of this invention have little or no activity as terrestrial herbicides, so their activity as aquatic herbicides is most unexpected.

The compounds useful in the novel method and compositions disclosed herein are readily prepared using starting materials and procedures well known to those skilled in the art.

The intermediate 2-amino-5-substituted-1,3,4-thiadiazoles are prepared by methods disclosed in U.S. Pat. No. 3,669,982 (June 13, 1972), which disclosure is hereby incorporated herein and made a part of this application.

The thiadiazol-2-ylurea compounds are obtained by allowing the intermediate aminothiadiazole compounds to react with an arylisocyanate according to procedures well known in the art.

The preparation of the intermediate compounds is exemplified by the following descriptions and preparations.

One of the starting materials, 2-amino-5-trifluoromethyl-1,3,4-thiadiazole, is prepared by allowing thiosemicarbazide to react with trifluoroacetic acid in polyphosphoric acid as solvent. The mixture is stirred mechanically and gradually warmed, during which time a vigorous exothermic reaction takes place at about 70° C., following which the reaction mixture is slowly heated to and held at a temperature of about 110° C., for a time suitable for bringing the reaction to completion. Such time is about 1.5 hours. The reaction product mixture is worked up by pouring it onto ice. After the ice is melted, the solid material is filtered off. It is recrystallized from a suitable solvent, such as aqueous ethanol, to yield product having a melting point of about 225°–230° C., and identified by elemental analyses and NMR spectrum as 2-amino-5-trifluoromethyl-1,3,4-thiadiazole.

Another of the starting materials, 2-amino-5-hexylthio-1,3,4-thiadiazole, is readily obtained by allowing commercially-available 2-amino-5-mercapto-1,3,4-thiadiazole to react with 1-bromohexane in alcoholic potassium hydroxide at reflux temperature for about an hour. The reaction mixture is cooled and allowed to stand overnight. The precipitated solids are filtered off and washed with ethyl acetate. The filtrate is concentrated in vacuo to remove the solvent, leaving an oil. The oil is extracted with ethyl acetate, the extracts washed with water and dried over anhydrous sodium sulfate. The drying agent is filtered off and the ethyl acetate solution concentrated to dryness. The residue is washed with hexane and identified by melting point as 2-amino-5-hexylthio-1,3,4-thiadiazole.

Another starting material, 2-amino-5-nitro-1,3,4-thiadiazole, is prepared by the nitration of commercially-available 2-amino-1,3,4-thiadiazole, according to the procedure of U.S. Pat. No. 2,708,671 (1955) [C.A. 49, 15252a (1955)].

Yet another starting material, 2-amino-5-chloro-1,3,4-thiadiazole, is prepared following the procedure of Stolle and Fehrenbach, J. prakt. Chem. [2] 122, 303 (1929).

The related 2-amino-5-bromo-1,3,4-thiadiazole is prepared by allowing commercially-available 2-amino-1,3,4-thiadiazole to react with bromine. The bromine is added dropwise to a mixture of the thiadiazole and sodium acetate in glacial acetic acid at room temperature, followed by warming of the reaction mixture on the steam bath for about an hour. The reaction is worked up by pouring onto ice and filtering off the solids which precipitate. The solids are then suspended in water and the pH adjusted to about 11. The insoluble solid is filtered off and washed with water. The solid has a melting point of about 193°–195° C., and is identified as 2-amino-5-bromo-1,3,4-thiadiazole.

Another starting thiadiazole, 2-amino-5-methyl-1,3,4-thiadiazole, is prepared according to the procedure of Freund and Meinecke, Chem. Ber. 29, 2511 at 2516 (1896). Following that procedure, acetyl chloride is allowed to react with thiosemicarbazide to yield 2-amino-5-methyl-1,3,4-thiadiazole.

In general, the preparation of the 5-substituted-1,3,4-thiadiazol-2-ylurea compounds useful in the novel method of this invention is accomplished by allowing the above-described 2-amino-5-substituted-1,3,4-thiadiazoles to react with a suitable arylisocyanate.

Another method of preparing the 5-substituted-1,3,4-thiadiazol-2-ylurea compounds is by allowing an alkyl or aryl N-(5-substituted-1,3,4-thiadiazol-2-yl)carbamate to react with a suitably substituted aniline at the reflux temperature of an inert solvent for a time sufficient to complete the reaction. For example, phenyl N-(5-trifluoromethyl-1,3,4-thiadiazol-2-yl)carbamate is allowed to react with 3,4,5-trichloroaniline in refluxing toluene for about 12 hours. The reaction mixture is cooled, the solid which precipitates is filtered off and purified by recrystallization from a solvent such as commercial absolute alcohol to yield product identified by elemental analyses and infrared and NMR spectra as 1-(3,4,5-trichlorophenyl)-3-[5-trifluoromethyl)-1,3,4-thiadiazol-2-yl]urea.

The majority of the arylisocyanate compounds are commercially available. Those arylisocyanates not commercially available can readily be prepared according to the general procedure wherein an appropriately substituted aryl amine is allowed to react at reflux temperature with phosgene in a suitable solvent, such as ethyl acetate. Such preparation is exemplified as follows: $\alpha,\alpha,\alpha,\alpha',\alpha',\alpha'$-Hexafluoro-3,5-xylylamine is allowed to react with phosgene, in ethyl acetate as solvent, at reflux temperature for about 2 hours. The reaction product mixture is concentrated to dryness in vacuo, leaving a residue. The residue is identified by infrared spectrum as $\alpha,\alpha,\alpha,\alpha',\alpha',\alpha'$-hexafluoro-3,5-xylylisocyanate.

Utilizing reactants synthesized as described hereinbefore, the thiadiazol-2-ylureas used in the novel method of this invention are prepared by the following general procedure. The 2-amino-5-substituted-1,3,4-thiadiazole is dissolved or suspended in a suitable solvent such as benzene. Other suitable solvents include toluene, xylene, and the like. A substituted arylisocyanate is added to the solution or suspension and the mixture is refluxed for a period of time sufficient to complete the reaction. Such period of time is suitably from about 30 minutes to about 2 hours. At the end of the reaction time, the reaction product mixture is cooled and filtered to recover the solid material. This solid material is recrystallized from a suitable solvent such as commercial absolute ethanol. The product obtained is identified by infrared and/or NMR spectra and elemental analyses.

Thus, for example, 2-amino-5-trifluoromethyl-1,3,4-thiadiazole is allowed to react with m-tolylisocyanate in benzene at reflux temperature for about one-half hour.

The reaction product is cooled and the solid which precipitates is filtered off. The solid is purified by recrystallization from a suitable solvent, such as commercial absolute ethanol, to yield product having a melting point of about 233°–235° C. The product is identified by elemental analyses and infrared and NMR spectra as 1-(m-tolyl)-3-[5-(trifluoromethyl)-1,3,4-thiadiazol-2-yl]urea.

The preparation of 1,3,4-thiadiazol-2-ylureas substituted in the 5-position with an alkylsulfonyl grouping is readily accomplished by oxidation of the precursor 5-alkylthio compound using conventional methods, e.g., hydrogen peroxide in acetic acid.

Thus, illustratively, 1-(3,4-dichlorophenyl)-3-[5-(hexylthio)-1,3,4-thiadiazol-2-yl]urea is oxidized in acetic acid solution using hydrogen peroxide, to yield 1-(3,4-dichlorophenyl)-3-[5-(hexylsulfonyl)-1,3,4-thiadiazol-2-yl]urea, identified by elemental analyses and NMR spectrum.

The starting materials from which the thiadiazol-2-ylureas are synthesized are obtained according to the teachings of the following Preparations.

PREPARATION 1

2-Amino-5-trifluoromethyl-1,3,4-thiadiazole

To 54.7 g. (0.6 mole) of thiosemicarbazide in 135 g. of polyphosphoric acid was added 96 g. (0.84 mole) of trifluoroacetic acid. The mixture was stirred mechanically under a reflux condenser and gradually warmed. Vigorous refluxing took place at about 70° C., which refluxing gradually moderated. The reaction mixture was then warmed to and held at a temperature of about 110° C. for about 1.5 hours. It was then poured onto 1 kilogram of ice. After the ice melted, the white solid which had precipitated was filtered off, washed with water, and air-dried. The dried solid was recrystallized from aqueous ethanol to yield white platelets having a melting point of about 225°–230° C., identified by NMR spectrum and elemental analyses as 2-amino-5-trifluoromethyl-1,3,4-thiadiazole.

PREPARATION 2

Pentachlorophenylisocyanate

To 250 ml. of a saturated solution of phosgene in ethyl acetate was added 25 g. of pentachloroaniline in 75 ml. of tetrahydrofuran. The reaction mixture was heated at reflux for about 1.5 hours. The mixture was cooled and concentrated to dryness in vacuo, leaving a tan solid. The tan solid was identified by infrared spectrum as pentachlorophenylisocyanate and was used without further purification.

PREPARATION 3

$\alpha,\alpha,\alpha,\alpha',\alpha',\alpha'$-Hexafluoro-3,5-xylylisocyanate To 250 ml. of a saturated solution of phosgene in ethyl acetate was added a solution of 15 g. of $\alpha,\alpha,\alpha,\alpha',\alpha',\alpha'$-hexafluoro-3,5-xylylamine in 50 ml. of ethyl acetate. The reaction mixture was refluxed for about 2 hours. The mixture was cooled and concentrated to dryness in vacuo, leaving a white semisolid. The solid was identified by infrared spectrum as $\alpha,\alpha,\alpha,\alpha',\alpha',\alpha'$-hexafluoro-3,5-xylylisocyanate. The material was used without further purification.

PREPARATION 4

2-Amino-5-bromo-1,3,4-thiadiazole

A solution of 34.0 g. (0.31 mole) of 2-amino-1,3,4-thiadiazole and 122 g. (1.49 moles) of sodium acetate was prepared in 130 ml. of glacial acetic acid. This mixture was stirred and 52.8 g. (0.65 mole) of bromine, dissolved in 170 ml. of glacial acetic acid, was added dropwise. The reaction mixture developed an orange color during the addition of the bromine. The reaction mixture was heated on the steam bath for about 1 hour. At the end of that time, the reaction mixture was poured onto ice and the solid which precipitated was recovered by filtration. The solid was suspended in water and the mixture adjusted to about pH 11 with aqueous ammonium hydroxide. The mixture was filtered and the solid on the Buchner funnel was washed with water. The solid had a melting point of about 193°–195° C. and was identified as 2-amino-5-bromo-1,3,4-thiadiazole.

PREPARATION 5

2-Amino-5-hexylthio-1,3,4-thiadiazole

A 1 normal alcoholic potassium hydroxide solution was prepared from 17.7 g. of potassium hydroxide and 270 ml. of ethanol. To the solution was added 20.0 g. (0.15 mole) of 2-amino-5-mercapto-1,3,4-thiadiazole, and when solution had been accomplished there was added dropwise 24.8 g. (0.15 mole) of 1-bromohexane. When addition was complete, the reaction mixture was refluxed for about 1 hour, during which time a solid precipitated. The reaction product mixture was cooled and allowed to stand overnight at ambient room temperature. The reaction product mixture was filtered and the solid collected on the Buchner funnel was washed with ethyl acetate. The solid was discarded. The filtrate was concentrated in vacuo to yield an oil. The oil was extracted with ethyl acetate, the ethyl acetate extract washed with water, and the water washings discarded. The ethyl acetate solution was dried over anhydrous sodium sulfate. The drying agent was filtered off. The ethyl acetate solution was concentrated in vacuo to yield a residue which had a melting point of about 97°–100° C., and which was identified as 2-amino-5-hexylthio-1,3,4-thiadiazole.

PREPARATION 6

Phenyl N-(5-trifluoromethyl-1,3,4-thiadiazol-2-yl)carbamate

A suspension of 20 g. (0.12 mole) of 2-amino-5-trifluoromethyl-1,3,4-thiadiazole in 400 ml. of benzene was prepared. To the suspension was added dropwise a solution of 20.3 g. (0.13 mole) of phenyl chloroformate in 25 ml. of benzene. When addition was complete, the reaction mixture was refluxed for about 4 hours, by which time complete solution was attained. The reaction mixture was cooled. A precipitate formed which was filtered off, washed with hexane, and discarded. The filtrate was concentrated in vacuo to leave a residue having a melting point of about 183°–185° C., and which was identified by infrared spectrum as phenyl N-(5-trifluoromethyl-1,3,4-thiadiazol-2-yl)carbamate. The material was used without further purification.

PREPARATION 7

2-Nitro-4-trifluoromethylphenylisocyanate

To 300 ml. of a saturated solution of phosgene in ethyl acetate was added a solution of 25 g. of 2-nitro-4-trifluoromethylaniline in 75 ml. of ethyl acetate. The mixture was refluxed for about 1.5 hours. The mixture was cooled and concentrated to dryness in vacuo to yield a yellow oil. The oil was identified as 2-nitro-4-trifluoromethylphenylisocyanate. It was used without further purification.

The syntheses of the thiadiazol-2-ylureas useful in the novel method of this invention are exemplified as follows:

EXAMPLE 1

1-(m-Tolyl)-3-[5-(trifluoromethyl)-1,3,4-thiadiazol-2-yl]urea

To 5 g. of 2-amino-5-trifluoromethyl-1,3,4-thiadiazole in 130 ml. of benzene was added 5 g. of m-tolylisocyanate. The mixture was refluxed for about 30 minutes. The reaction product mixture was cooled and filtered to recover the solid material. This solid was recrystallized from commercial absolute ethanol to yield white crystals having a melting point of about 233°–235° C., identified by infrared and NMR spectra, and elemental analyses as 1-(m-tolyl)-3-[5-(trifluoromethyl)-1,3,4-thiadiazol-2-yl]urea (Compound 1).

Following the same general procedure of Example 1 and using appropriate starting materials, the following additional compounds were prepared and identified by elemental analyses and NMR spectrum:

2. 1-(3,4-Dichlorophenyl)-3-[5-(trifluoromethyl)-1,3,4-thiadiazol-2-yl]urea, m.p. 240°–242° C.
3. 1-(p-Chlorophenyl)-3-[5-(trifluoromethyl)-1,3,4-thiadiazol-2-yl]urea, m.p. 276°–278° C.
4. 1-(o-Tolyl)-3-[5-(trifluoromethyl)-1,3,4-thiadiazol-2-yl]urea, m.p. 225°–226° C.
5. 1-(1,3,4-Thiadiazol-2-yl)-3-($\alpha,\alpha,\alpha$-trifluoro-p-tolyl)urea, m.p. 280° C.
6. 1-(3,4-Dichlorophenyl)-2-thio-3-[5-(trifluoromethyl)-1,3,4-thiadiazol-2-yl]urea, m.p. 202°–204° C.
7. 1-(3,4Dichlorophenyl)-3-[5-(trifluoromethyl)-1,3,4-thiadiazol-2-yl]urea, isolated as the hemicopper (2+) salt, m.p. 240° C.
8. 1-(3,4-Dichlorophenyl)-3-(5-nitro-1,3,4-thiadiazol-2-yl)urea, m.p. 250°–252° C.
   1-(m-Nitrophenyl)-3-[5-(trifluoromethyl)-1,3,4-thiadiazol-2-yl]urea, m.p. 215°–217° C.
10. 1-Phenyl-3-[5-(trifluoromethyl)-1,3,4-thiadiazol-2-yl]urea, m.p. 251°–253° C.
11. 1-[5-(Trifluoromethyl)-1,3,4-thiadiazol-2-yl]-3-($\alpha,\alpha,\alpha$-trifluoro-m-tolyl)urea, m.p. 217°–218° C.
12. 1-(m-Chlorophenyl)-3-[5-(trifluoromethyl)-1,3,4-thiadiazol-2-yl]urea, m.p. 237°–240° C.
13. 1-(p-Methoxyphenyl)-3-[5-(trifluoromethyl)-1,3,4-thiadiazol-2-yl]urea, m.p. 227°–229° C.
14. 1-(p-Nitrophenyl)-3-[5-(trifluoromethyl)-1,3,4-thiadiazol-2-yl]urea, m.p. 282°–284° C.
15. 1-[5-(Trifluoromethyl)-1,3,4-thiadiazol-2-yl]-3-($\alpha,\alpha,\alpha$-trifluoro-p-tolyl)urea, m.p. 222°–225° C.
16. 1-(p-Tolyl)-3-[5-(trifluoromethyl)-1,3,4-thiadiazol-2-yl]urea, m.p. 250°–252° C.
17. 1-($\alpha,\alpha,\alpha$-Trifluoro-2-nitro-p-tolyl)-3-[5-(trifluoromethyl)-1,3,4-thiadiazol-2-yl]urea, m.p. 197°–202° C.
18. 1-(3,4-Dichlorophenyl)-3-[5-(hexylthio)-1,3,4-thiadiazol-2-yl]urea, m.p. 206°–208° C.
19. 1-(2,4-Dichlorophenyl)-3-[5-(trifluoromethyl)-1,3,4-thiadiazol-2-yl]urea, m.p. 258°–260° C.
20. 1-(o-Chlorophenyl)-3-[5-(trifluoromethyl)-1,3,4-thiadiazol-2-yl]urea, m.p. 255°–257° C.
21. 1-(o-Fluorophenyl)-3-[5-(trifluoromethyl)-1,3,4-thiadiazol-2-yl]urea, m.p. 239°–241° C.
22. 1-[5-(Trifluoromethyl)-1,3,4-thiadiazol-2-yl]-3-($\alpha,\alpha,\alpha$-trifluoro-o-tolyl)urea, m.p. 171°–172° C.
23. 1-(p-Fluorophenyl)-3-[5-(trifluoromethyl)-1,3,4-thiadiazol-2-yl]urea, m.p. 257°–259° C.
24. 1-(Pentachlorophenyl)-3-[5-(trifluoromethyl)-1,3,4-thiadiazol-2-yl]urea, m.p. 257°–260° C.
25. 1-(3-Chloro-4-fluorophenyl)-3-[5-(trifluoromethyl)-1,3,4-thiadiazol-2-yl]urea, m.p. 228°–230° C.
26. 1-(2,6-Dichlorophenyl)-3-[5-(trifluoromethyl)-1,3,4-thiadiazol-2-yl]urea, m.p. 228°–231° C.
27. 1-(2,3-Dichlorophenyl)-3-[5-(trifluoromethyl)-1,3,4-thiadiazol-2-yl]urea, m.p. 244°–247° C.
28. 1-(4-Chloro-$\alpha,\alpha,\alpha$-trifluoro-m-tolyl)-3-[5-(trifluoromethyl)-1,3,4-thiadiazol-2-yl]urea, m.p. 232°–235° C.
29. 1-(5-Chloro-1,3,4-thiadiazol-2-yl)-3-(3,4-dichlorophenyl)urea, m.p. 246°–248° C.
30. 1-(3,4-Dichlorophenyl)-3-(5-phenyl-1,3,4-thiadiazol-2-yl)urea, m.p. >300° C.
31. 1-(3,5-Dichlorophenyl)-3-[5-(trifluoromethyl)-1,3,4-thiadiazol-2-yl]urea, m.p. 262°–265° C.
32. 1-(o-Nitrophenyl)-3-[5-(trifluoromethyl)-1,3,4-thiadiazol-2-yl]urea, m.p. 195°–197° C.
33. 1-(m-Fluorophenyl)-3-[5-(trifluoromethyl)-1,3,4-thiadiazol-2-yl]urea, m.p. 218°–220° C.
34. 1-(m-Methoxyphenyl)-3-[5-(trifluoromethyl)-1,3,4-thiadiazol-2-yl]urea, m.p. 211°–212° C.
35. 1-($\alpha,\alpha,\alpha,\alpha',\alpha',\alpha'$-Hexafluoro-3,5-xylyl)-3-[5-(trifluoromethyl)-1,3,4-thiadiazol-2-yl]urea, m.p. 224°–225° C.
36. 1-[5-(Trifluoromethyl)-1,3,4-thiadiazol-2-yl]-3-(3,4-xylyl)urea, m.p. 255°–257° C.
37. 1-(p-Cyanophenyl)-3-[5-(trifluoromethyl)-1,3,4-thiadiazol-2-yl]urea, m.p. 263°–267° C.
38. 1-(5-Bromo-1,3,4-thiadiazol-2-yl)-3-(3,4-dichlorophenyl)urea, m.p. 246°–248° C.
39. 1-(3,4-Dichlorophenyl)-3-[5-(pentafluoroethyl)-1,3,4-thiadiazol-2-yl]urea, m.p. 214°–216° C.
40. 1-(3,4-Dichlorophenyl)-3-[5-(1,1-dimethyloctyl)-1,3,4-thiadiazol-2-yl]urea, m.p. 182°–184° C.
41. 1-(3,4-Dichlorophenyl)-3-(5-methyl-1,3,4-thiadiazol-2-yl)yrea, m.p. 272°–274° C.
42. 1-(5-Methyl-1,3,4-thiadiazol-2-yl)-3-(p-nitrophenyl)urea, m.p. 282° C. (dec.).

EXAMPLE 43

1-(3,4,5-Trichlorophenyl)-3-[5-(trifluoromethyl)-1,3,4-thiadiazol-2-yl]urea

A mixture of 2.89 g. of phenyl N-(5-trifluoromethyl-1,3,4-thiadiazol-2-yl)carbamate, 3.92 g. of 3,4,5-trichloroaniline, and 100 ml. of toluene was refluxed for about 12 hours. At the end of that time, the reaction mixture was cooled and the solid which precipitated was filtered off. The solid was recrystallized three times from commercial absolute ethanol to yield white crystals having a melting point of about 296°–300° C. The crystalline product was identified by elemental analyses and infrared and NMR spectra as 1-(3,4,5-trichlorophenyl)-3-[5-(trifluoromethyl)-1,3,4-thiadiazol-2-yl]urea.

EXAMPLE 44

1-(3,4-Dichlorophenyl)-3-[5-(hexylsulfonyl)-1,3,4-thiadiazol-2-yl]urea

A solution of 6.0 g. (0.015 mole) of 1-(3,4-dichlorophenyl)-3-[5-(hexylthio)-1,3,4-thiadiazol-2-yl]urea (Example 18) was prepared in 30 ml. of glacial acetic acid. The mixture was heated to about 85°–90° C. and 4.08 g. (0.036 mole) of 30 percent hydrogen peroxide was added dropwise. After addition was complete, the temperature of the reaction mixture was maintained at about 85°–90° C. for an additional 1.5 hours. The reaction mixture was then cooled and poured onto ice. A precipitate formed which was filtered off and washed with water. The solid thus obtained was recrystallized from a mixture of ethyl acetate and normal hexane to yield product having a melting point of about 204°–206° C., and identified by elemental analyses and NMR spectrum as 1-(3,4-dichlorophenyl)-3-[5-(hexylsulfonyl)-1,3,4-thiadiazol-2-yl]urea.

The novel method of this invention is practiced by adding the compounds coming within the scope of the generic formula, supra, to the water containing the aquatic weeds. The compounds may be applied as dusts when admixed with a powdered solid carrier such as any one or more of the various mineral silicates, e.g. mica, talc, pyrophyllite, and clays. The compounds may be mixed with surface-active dispersing agents to form herbicidal concentrates to facilitate dispersion in water and to improve the wetting properties when used as sprays. If desired, the compounds may be mixed with a powdered solid carrier together with a surface-active dispersing agent so that a wettable powder may be obtained which may be applied directly or which may be shaken up with water to make an aqueous dispersion for application in that form. The compounds may be dissolved in an oil such as a hydrocarbon or chlorinated hydrocarbon oil, and the oil solution of the chemical dispersed in water with the aid of a surface-active dispersing agent to give a sprayable aqueous dispersion. Such surface-active dispersing agents may be anionic, nonionic, or cationic surface-active agents. Such surface-active agents are well known and reference is made to Hoffmann et al., U.S. Pat. No. 2,614,916, columns 2–4, for detailed examples of the same. The compounds disclosed as useful in the present invention may be applied by the aerosol method. Solutions for the aerosol treatment may be prepared by dissolving the compound directly in the aerosol carrier, which is a liquid under pressure, but which is a gas at ordinary temperature (e.g. 20° C.) and atmospheric pressure, or the aerosol solution may be prepared by first dissolving the compound in a less volatile solvent, and then admixing such solution with the highly volatile liquid aerosol carrier.

The invention is practiced by adding to the water a sufficient amount of the compound that a concentration of from about 1 to about 10 parts per million is obtained, preferably sufficient compound to provide a concentration of from about 2 to about 10 parts per million.

The optimum concentration for any specific control problem varies with the temperature, the species to be controlled, the sensitivity of the fish life, and the shape of the water body to be treated. At higher water temperatures, less compound is generally required for a given degree of control than is needed at lower temperatures.

In considering the treatment of moving streams for the purpose of destroying flora fixed therein, special account must be taken of the fact that the treatment chemicals will pass over the area to be treated and that the concentration during the contact period is dependent upon the water flow rate, the rate of chemical addition, and the period of addition.

The novel herbicidal method and compositions are illustrated by the following experiments.

Experiment 1

The following method was used in the laboratory to evaluate the aquatic herbicidal properties of the compounds disclosed herein.

Thus, in the first test, the plants used were coontail, *Ceratophyllum demersun* L.; Florida elodea, *Hydrilla verticillata* (L.F.); and duckweed, *Lemna minor* L. The plants were prepared by cutting four-inch terminal sprigs of the coontail and elodea, and selecting approximately enough duckweed to just cover the surface of the water in a 10 ml. beaker (approximately 30 plants). The coontail, elodea, and duckweed were then placed in beakers containing 750 ml. of dechlorinated water containing the compounds.

The compounds for this test were formulated in the following manner. Seventeen mg. of compound was weighed into a 12 ml. disposable vial. To the vial containing the compound was added 1 ml. of acetone followed by 10 ml. of aqueous 0.1 percent polyoxyethylene sorbitan monooleate. This stock solution was then pipetted into the beakers at volumes of 0.45 ml. and 4.55 ml., to obtain concentrations of 1 and 10 ppm., respectively, of test compound in 750 ml. of water.

Observations of the effect of the compounds on the plants were made over a seven-day period. The scale for rating the aquatic herbicidal activity of the compounds was on a basis of 1–5, as follows:

1 = no effect
2 = slight effect
3 = moderate effect
4 = heavy effect
5 = complete kill The results of the test are recorded in Table 1, which follows.

In Table 1, column 1 lists the test compounds, each identified by the operating example number of the compound; Column 2 lists the rate of application of the test compounds in parts per million (ppm.); Columns 3, 4, and 5 list the herbicidal activity of the test compounds against the aquatic plants used in the tests.

Table 1

| Compound | Appln. Rate ppm. | Hydrilla | Coontail | Duckweed |
|---|---|---|---|---|
| 1 | 10 | 5 | 4 | 4 |
|   | 1  | — | — | — |
| 2 | 10 | 5 | 5 | 5 |
|   | 1  | 4 | 3 | 1 |
| 3 | 10 | 5 | 1.5 | 3.5 |
|   | 1  | 4.5 | 1.5 | 1 |
| 4 | 10 | 5 | 1 | 1 |
|   | 1  | — | — | — |

Table 1-continued

| Compound | Appln. Rate ppm. | Hydrilla | Coontail | Duckweed |
|---|---|---|---|---|
| 5 | 10 | 5 | 2 | 1 |
|  | 1 | — | — | — |
| 6 | 10 | 5 | 3 | 1 |
|  | 1 | — | — | — |
| 7 | 10 | 5 | 4 | 2 |
|  | 1 | — | — | — |
| 8 | 10 | 2 | 3 | 2 |
|  | 1 | — | — | — |
| 9 | 10 | 5 | 3.5 | 2 |
|  | 1 | 1.5 | 1 | 1 |
| 10 | 10 | 5 | 1 | 3 |
|  | 1 | 2.5 | 1 | 1 |
| 11 | 10 | 5 | 1 | 4 |
|  | 1 | 4.5 | 3 | 2.5 |
| 12 | 10 | 5 | 1 | 4.5 |
|  | 1 | 4.5 | 1.5 | 2 |
| 13 | 10 | 5 | 1 | 1 |
|  | 1 | 4 | 1 | 2 |
| 14 | 10 | 4 | 1 | 1 |
|  | 1 | 1 | 1 | 1 |
| 15 | 10 | 4 | 1 | 3 |
|  | 1 | 3 | 3 | 2 |
| 16 | 10 | 5 | 2 | 1 |
|  | 1 | 5 | 2 | 1 |
| 17 | 10 | 5 | 4 | 2 |
|  | 1 | 1 | 1 | 1 |
| 18 | 10 | 1 | 1 | 1 |
|  | 1 | 2 | 4 | — |
| 19 | 10 | 5 | 3 | 1 |
|  | 1 | — | — | — |
| 20 | 10 | 4 | 2.5 | 1.5 |
|  | 1 | — | — | — |
| 21 | 10 | 5 | 3 | 2 |
|  | 1 | — | — | — |
| 22 | 10 | 5 | 3 | 2 |
|  | 1 | — | — | — |
| 23 | 10 | 5 | 1 | 4 |
|  | 1 | — | — | — |
| 24 | 10 | 5 | 4 | 5 |
|  | 1 | — | — | — |
| 25 | 10 | 5 | 4 | 5 |
|  | 1 | — | — | — |
| 26 | 10 | 4 | 3 | 2 |
|  | 1 | — | — | — |
| 27 | 10 | 5 | 4 | 3 |
|  | 1 | — | — | — |
| 28 | 10 | 5 | 4 | 3 |
|  | 1 | — | — | — |
| 29 | 10 | 5 | 4 | 5 |
|  | 1 | — | — | — |
| 30 | 10 | 5 | 2 | 2 |
|  | 1 | — | — | — |
| 31 | 10 | 5 | 5 | 4 |
|  | 1 | — | — | — |
| 32 | 10 | 3 | 2 | 2 |
|  | 1 | — | — | — |
| 33 | 10 | 4 | 3 | 4 |
|  | 1 | — | — | — |
| 34 | 10 | 5 | 4 | 2 |
|  | 1 | — | — | — |
| 35 | 10 | 5 | 5 | 2 |
|  | 1 | — | — | — |
| 36 | 10 | 5 | 2 | 1 |
|  | 1 | — | — | — |
| 37 | 10 | 5 | 2 | 1 |
|  | 1 | — | — | — |
| 38 | 10 | 5 | 4 | 1 |
|  | 1 | — | — | — |
| 39 | 10 | 5 | 3 | 4 |
|  | 1 | — | — | — |
| 40 | 10 | 3 | 2 | 1 |
|  | 1 | — | — | — |
| 41 | 10 | 2 | 2 | 2 |
|  | 1 | — | — | — |
| 42 | 10 | 4 | 4 | 1 |
|  | 1 | — | — | — |
| 43 | 10 | 5 | 5 | 1 |
|  | 1 | — | — | — |
| 44 | 10 | 2 | 2 | — |
|  | 1 | 3 | 1 | — |

Experiment 2

In a second test in the laboratory, selected compounds from Experiment 1 were tested again against the same aquatic weeds, prepared the same way for testing as in Experiment 1. However, in this test, concentrations of 1, 2, and 4 ppm., respectively, of test compound were used.

The compounds for this test were formulated in the following manner. Ten mg. of compound was weighed into a 12 ml. disposable vial. To the vial containing the compound was added 1 ml. of acetone followed by 9 ml. of aqueous 0.1 percent polyoxyethylene sorbitan monooleate. This stock solution was then pipetted into beakers at volumes of 0.75 ml., 1.5 ml., and 3.0 ml., to obtain concentrations of test compound of 1, 2, and 4 ppm., respectively, in 750 ml. of water.

Observations of the effect of the compounds on the plants were made over a seven day period. The scale for rating the aquatic herbicidal activity of the compounds was the same as that used in Experiment 1.

The results of the test are recorded in Table 2, which follows.

In Table 2, Column 1 lists the test compound, each identified by the operating example number of the compound; Column 2 lists the rates of application of the test compounds in parts per million (ppm.); Columns 3, 4, and 5 list the herbicidal activity of the test compounds against the aquatic plants used in the tests.

Table 2

| Compound | Appln. Rate ppm. | Hydrilla | Coontail | Duckweed |
|---|---|---|---|---|
| 1 | 4 | 5 | 3 | 3 |
|  | 2 | 5 | 3 | 1 |
|  | 1 | — | — | — |
| 2 | 4 | 5 | 3 | 2 |
|  | 2 | 4 | 3 | 1 |
|  | 1 | 4 | 3 | 1 |
| 19 | 4 | 5 | 3 | 1 |
|  | 2 | 5 | 2 | 1 |
|  | 1 | — | — | — |
| 20 | 4 | 4 | 4 | 1 |
|  | 2 | 2 | 3 | 1 |
|  | 1 | — | — | — |
| 21 | 4 | 5 | 4 | 1 |
|  | 2 | 3 | 2 | 1 |
|  | 1 | — | — | — |
| 22 | 4 | 2 | 1 | 1 |
|  | 2 | 2 | 1 | 1 |
|  | 1 | — | — | — |
| 23 | 4 | 5 | 3 | 1 |
|  | 2 | 5 | 2 | 1 |
|  | 1 | — | — | — |
| 24 | 4 | 5 | 4 | 1 |
|  | 2 | 5 | 3 | 1 |
|  | 1 | — | — | — |
| 25 | 4 | 4 | 3 | 2 |
|  | 2 | 4 | 3 | 1 |
|  | 1 | — | — | — |
| 27 | 4 | 4 | 3 | 1 |
|  | 2 | 4 | 2 | 1 |
|  | 1 | — | — | — |
| 29 | 4 | 5 | 4 | 2 |
|  | 2 | 5 | 3 | 1 |
|  | 1 | 5 | 3 | 1 |
| 31 | 4 | 5 | 4 | 2 |
|  | 2 | 5 | 3 | 1 |
|  | 1 | — | — | — |
| 34 | 4 | 4 | 2 | 1 |
|  | 2 | 2 | 2 | 1 |
|  | 1 | — | — | — |
| 35 | 4 | 2 | 1 | 1 |
|  | 2 | 1 | 1 | 1 |
|  | 1 | — | — | — |
| 39 | 4 | 5 | 4 | 1 |
|  | 2 | 5 | 4 | 1 |
|  | 1 | — | — | — |

I claim:

1. A method of destroying aquatic weeds in water which comprises contacting the weeds with an herbicidally-effective amount of a compound of the formula

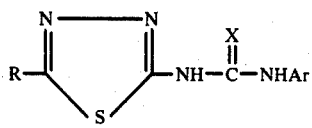

wherein
R is halo($C_1$–$C_2$)alkyl, phenyl, nitro, hexylthio, hexylsulfonyl, or halo;
Ar is phenyl, or phenyl having one or more substituents, up to five, selected from the group consisting of methyl, nitro, trifluoromethyl, methoxy, cyano, and halo; and
X is oxygen.

2. The method of claim 1 wherein the active compound is 1-(3,4-dichlorophenyl)-3-(5-trifluoromethyl-1,3,4-thiadiazol-2-yl)urea.

3. The method of claim 1 wherein the active compound is 1-(3-chloro-4-fluorophenyl)-3-(5-trifluoromethyl-1,3,4-thiadiazol-2-yl)urea.

4. The method of claim 1 wherein the active compound is 1-(5-chloro-1,3,4-thiadiazol-2-yl)-3-(3,4-dichlorophenyl)urea.

5. The method of claim 1 wherein the active compound is 1-(3,5-dichlorophenyl)-3-(5-trifluoromethyl-1,3,4-thiadiazol-2-yl)urea.

6. The method of claim 1 wherein the active compound is 1-(m-tolyl)-3-(5-trifluoromethyl-1,3,4-thiadiazol-2-yl)urea.

7. The method of claim 1 wherein the active compound is 1-(pentachlorophenyl)-3-(5-trifluoromethyl-1,3,4-thiadiazol-2-yl)urea.

8. The method of claim 1 wherein the active compound is 1-(3,4-dichlorophenyl)-3-[5-(pentafluoroethyl)-1,3,4-thiadiazol-2-yl]urea.

9. The method of claim 1 wherein the active compound is added to said water in an amount sufficient to give a concentration of from about 1 to about 10 parts per million parts of said water.

* * * * *